(12) United States Patent
Chen et al.

(10) Patent No.: US 9,115,041 B2
(45) Date of Patent: *Aug. 25, 2015

(54) PROCESS FOR THE PRODUCTION OF PARA-XYLENE

(71) Applicant: Chevron U.S.A. Inc., San Ramon, CA (US)

(72) Inventors: Cong-Yan Chen, Alameda, CA (US); Stephen J. Miller, San Francisco, CA (US); James N. Ziemer, Martinez, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/145,818

(22) Filed: Dec. 31, 2013

(65) Prior Publication Data

US 2014/0114106 A1 Apr. 24, 2014

Related U.S. Application Data

(60) Division of application No. 14/055,671, filed on Oct. 16, 2013, which is a continuation of application No. 12/845,618, filed on Jul. 28, 2010, now abandoned.

(51) Int. Cl.
*C07C 5/32* (2006.01)
*C10G 47/00* (2006.01)
*C10G 35/06* (2006.01)
*C07C 5/373* (2006.01)
*C07C 5/41* (2006.01)

(52) U.S. Cl.
CPC ............... *C07C 5/373* (2013.01); *C07C 5/322* (2013.01); *C07C 5/41* (2013.01); *C07C 2529/40* (2013.01)

(58) Field of Classification Search
CPC ............ C07C 5/32; C10G 47/00; C10G 35/06
USPC .......... 585/319, 418, 419, 422; 208/135, 137, 208/318, 107
See application file for complete search history.

(56) References Cited

U.S. PATENT DOCUMENTS 3,806,443 A * 4/1974 Maziuk ........................... 208/60

* cited by examiner

*Primary Examiner* — Thuan D Dang
(74) *Attorney, Agent, or Firm* — E. Joseph Gess; Michael D. Ross; Melissa M. Hayworth

(57) ABSTRACT

A reforming process using a medium pore zeolite under conditions to facilitate the conversion of $C_8$ paraffinic compounds to para-xylene is provided. Para-xylene is produced at greater than thermodynamic equilibrium concentrations using the process.

27 Claims, 1 Drawing Sheet

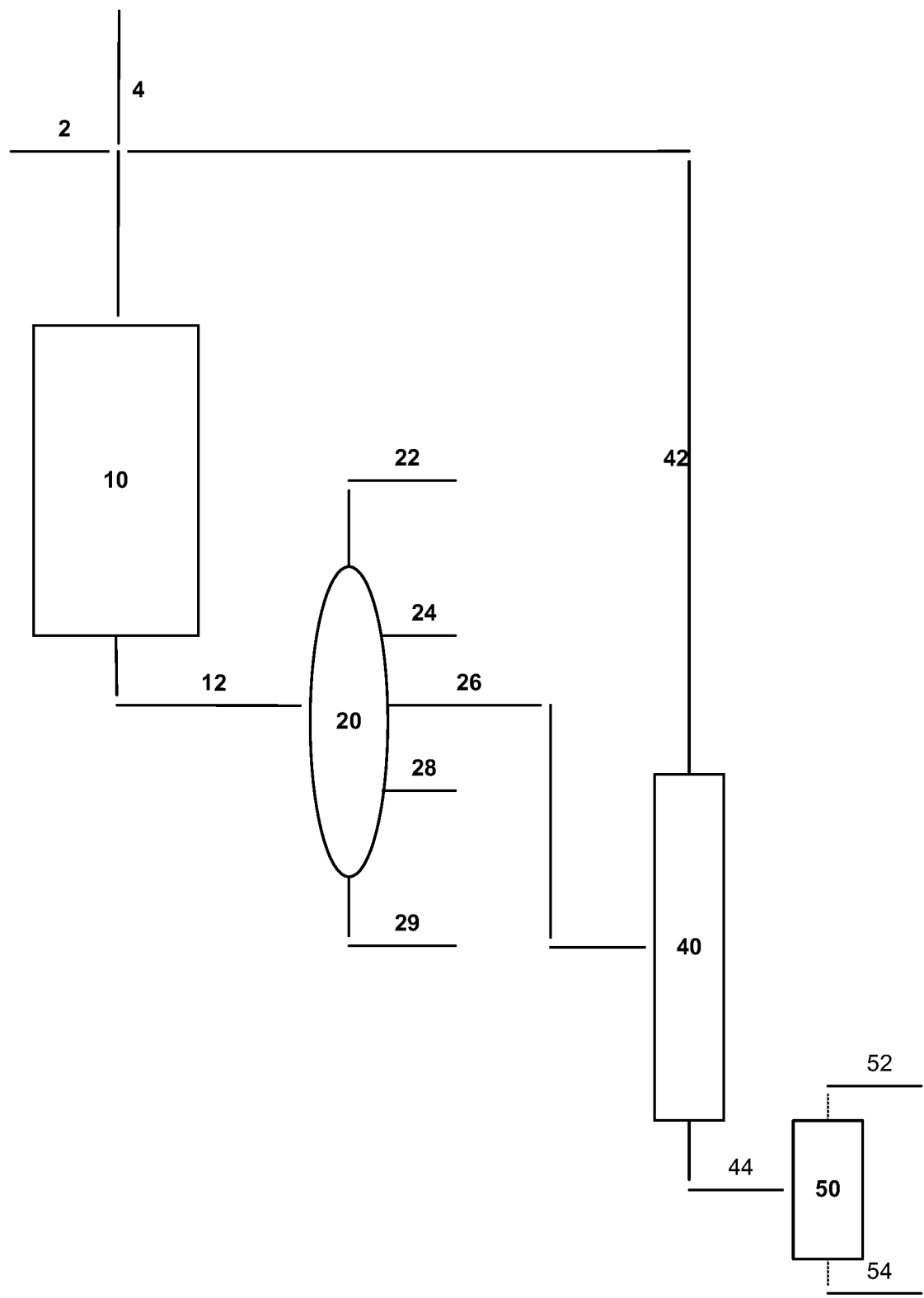

PROCESS FOR THE PRODUCTION OF PARA-XYLENE

REFERENCE TO RELATED APPLICATION

The present application is a divisional of U.S. application Ser. No. 14/055,671, filed Oct. 16, 2013 and entitled "Process for the Production of Para-Xylene", which is a continuation of U.S. application Ser. No. 12/845,618, filed Jul. 28, 2010, also entitled "Process for the Production of Para-Xylene." Both of these priority applications are herein incorporated by reference in their entirety.

FIELD OF THE INVENTION

The present invention provides a process for the production of para-xylene from a C8 containing paraffinic feedstock. A shape selective catalyst comprising a medium pore zeolite with a silica to alumina ratio of at least 40:1 is used during the catalytic reaction.

BACKGROUND

Catalytic reforming is one of the basic petroleum refining processes for upgrading light hydrocarbon feedstocks, frequently referred to as naphtha feedstocks. Products from catalytic reforming can include high octane gasoline useful as automobile fuel, aromatics (for example benzene, toluene, xylenes and ethylbenzene), and/or hydrogen. Reactions typically involved in catalytic reforming include dehydrocyclization, isomerization and dehydrogenation of naphtha range hydrocarbons, with dehydrocyclization and dehydrogenation of linear and slightly branched alkanes and dehydrogenation of cycloparaffins leading to the production of aromatics. Dealkylation and hydrocracking during catalytic reforming are generally undesirable due to the low value of the resulting light hydrocarbon products.

Xylene is composed of three different isomers, para-xylene (PX), meta-xylene (MX), and ortho-xylene (OX). Of the xylene isomers, para-xylene (PX) is of particular value since it is useful in the manufacture of terephthalic acid which is an intermediate in the manufacture of synthetic fibers. One current method for producing para-xylene is using naphtha reforming where mixed aromatics are produced. An aromatic containing stream can be separated and the stream used as a feedstock for the production of para-xylene. Generally, para-xylene is produced along with other xylene isomers and toluene. Purified toluene may be selectively or non-selectively disproportionated to produce para-xylene and benzene. Para-xylene may also be produced from mixed xylenes by isomerization followed by separation of the para-xylene from the meta and ortho isomers.

One known method for producing xylenes involves the alkylation of toluene with methanol over a solid acid catalyst. The alkylation of toluene with methanol over cation-exchanged zeolite Y has been described by, for example, Yashima et al. in the Journal of Catalysis 16, 273-280 (1970). Under optimized reaction conditions, the amount of para-xylene produced was approximately 50 wt % of the xylene product mixture.

U.S. Pat. Nos. 7,119,239 and 7,176,339 disclose a process for the production of xylenes from reformate. The process is carried out by methylating, under conditions effective for the methylation, the benzene/toluene present in the reformate, to produce a resulting product having a higher xylenes content than the reformate. Greater than equilibrium amounts of para-xylene can be produced by the process. U.S. Pat. No. 7,186,873 discloses a process for the production of xylenes from reformate by reactive distillation. The process is carried out by methylating the benzene/toluene present in the reformate in a reactive distillation zone and under reactive distillation conditions to produce a resulting product having a higher xylenes content than the reformate. Greater than equilibrium amounts of para-xylene can be produced by the process.

Given the higher demand for para-xylene as compared with other xylene isomers, there is significant commercial interest in maximizing para-xylene production from any given source of $C_8$ feedstocks. However, there are two major technical challenges in achieving this goal of maximizing para-xylene yield. Firstly, the four $C_8$ aromatic compounds, para-xylene, meta-xylene, ortho-xylene, and ethylbenzene, are usually present in concentrations dictated by thermodynamic equilibria, where meta-xylene comprises about 60 wt. %, para-xylene about 14 wt. %, ortho-xylene about 9 wt. %, and ethylbenzene about 17 wt. % of the $C_8$ aromatic compounds. As a result, the para-xylene yield is limited from any refinery $C_8$ stream unless additional processing steps are used to increase the amount of para-xylene and/or to improve the para-xylene recovery efficiency. Secondly, the $C_8$ aromatics are difficult to separate due to their similar chemical structures and physical properties and identical molecular weights.

A variety of methods are known to increase the concentration of para-xylene in a $C_8$ aromatics product stream. These methods normally involve recycling the product stream between a separation step, in which at least part of the para-xylene is recovered to produce a para-xylene-depleted stream, and a xylene isomerization step, in which the para-xylene content of the para-xylene-depleted stream is returned back towards equilibrium concentration, typically by contact with a molecular sieve catalyst. However, the commercial utility of these methods depends on the efficiency, cost effectiveness and rapidity of the separation step which, as discussed above, is complicated by the chemical and physical similarity of the different $C_8$ isomers.

A variety of methods are known in the art to purify para-xylene from less valuable xylene isomers and ethylbenzene. Fractional distillation is a commonly used method for separating different components in chemical mixtures. However, it is difficult to use conventional fractional distillation technologies to separate ethylbenzene (EB) and the different xylene isomers because the boiling points of the four $C_8$ aromatics fall within a very narrow range, namely from about 136° C. to about 144° C. In particular, the boiling points of para-xylene and EB are about 2° C. apart, whereas the boiling points of para-xylene and meta-xylene are only about 1° C. apart. As a result, large equipment, significant energy consumption, and/or substantial recycles would be required for fractional distillation to provide effective $C_8$ aromatic separation. Another method for separating the para-xylene from other xylene isomers and ethylbenzene involves crystallizing the para-xylene. U.S. Pat. No. 5,811,629 discloses a process for purifying para-xylene from $C_8$ aromatics involving at least two crystallization stages as well as at least one recycle step and at least one additional separation step. The above described methods are time consuming and costly. It is desirable to increase the amount of para-xylene in the product stream so as to minimize the number of recycle and purification steps needed to obtain pure para-xylene product.

It has been found that the use of a low acidity medium pore zeolite catalyst with a silica to alumina ratio of at least about 40 to 1, increases the yield of para-xylene from a given $C_8$ paraffinic feedstock.

SUMMARY OF THE INVENTION

The present invention provides for process for producing para-xylene comprising the steps of: providing a $C_8$ containing feedstock, which contains at least 10 wt. % $C_8$ paraffinic hydrocarbons, to a reforming reaction zone that contains a reforming catalyst comprising a medium pore zeolite having a silica to alumina molar ratio of at least 200, and a crystallite size of less than 10 microns; contacting the $C_8$ containing feedstock under reforming reaction conditions in the reforming reaction zone to produce para-xylene and meta-xylene in a para-xylene to meta-xylene weight ratio is at least 0.9; and separating the para-xylene from the meta-xylene.

In another embodiment, the present invention provides process for producing para-xylene comprising the steps of: contacting a hydrocarbonaceous feed wherein at least 50 wt. % of said feed boils above 550° F., in a first reaction zone comprising a hydrocracking catalyst under hydrocracking conditions to form an effluent; separating the effluent into at least a C8 containing fraction comprising at least 10 wt. % C8 paraffinic hydrocarbons; providing the C8 containing fraction to a second reaction zone; contacting the C8 containing fraction under reforming reaction conditions with a reforming catalyst comprising a medium pore zeolite having a silica to alumina molar ratio of at least 200, a crystallite size of less than 10 microns and an alkali content of less than 5000 ppm in a second reaction zone to produce a product stream comprising para-xylene and meta-xylene wherein the para-xylene to meta-xylene ratio is at least 0.9; and separating the para-xylene from the product stream.

BRIEF DESCRIPTION OF THE DRAWINGS

FIG. 1 is a schematic diagram of one embodiment of the invention.

DETAILED DESCRIPTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The present invention relates to a process for increasing or maximizing the production and/or yield of para-xylene (PX) in chemical plants and refineries, where feedstocks comprising $C_8$ paraffinic compounds are separated, produced, and/or processed. The present invention also relates to a para-xylene containing product produced by such a process or in such a plant. In an embodiment, the process of the invention uses a naphtha boiling range feedstock comprising at least about 10 wt. % $C_8$ paraffinic hydrocarbons. In an embodiment, the feedstock can boil in the range of from about 50° F. to about 550° F. and more typically in the range of from about 70° F. to about 450° F.

The present invention provides for a process to make para-xylene from a $C_8$ containing paraffinic feedstock. In an embodiment, by "$C_8$ containing paraffinic feedstock" is meant a feedstock generally containing at least about 5 wt. % paraffinic $C_8$ hydrocarbons, more typically at least about 10 wt. % paraffinic $C_8$ hydrocarbons, and often at least about 12 wt. % paraffinic $C_8$ hydrocarbons, and even at least about 15 wt. % paraffinic $C_8$ hydrocarbons. In a separate embodiment, by "$C_8$ containing paraffinic feedstock" is meant a feedstock generally containing at least about 40 wt. % paraffinic $C_8$ hydrocarbons, and more typically at least about 50 wt. % $C_8$ paraffinic hydrocarbons and often at least about 60 wt. % $C_8$ paraffinic hydrocarbons. The $C_8$ containing paraffinic feedstock also generally contains less than 20 wt. % $C_{10}+$ hydrocarbons, more typically less than 10 wt. % $C_{10}+$ hydrocarbons, and often less than 5 wt. % $C_{10}+$ hydrocarbons and even less than 1 wt. % $C_{10+}$ hydrocarbons. In general, the presence of aromatics in the feed, including the $C_8$ isomers para-xylene, meta-xylene, ortho-xylene, and/or ethylbenzene is not detrimental to the process. For example, the feedstock can contain up to 1 wt. % para-xylene, up to 2 wt. % para-xylene, or up to even greater amounts of para-xylene. In embodiments, the feedstock contains in the range of 0 to 2 wt. % para-xylene.

Generally, the $C_8$ containing feedstock can be a straight run naphtha or fractions thereof or hydrocracker naphtha, e.g., a $C_8$ cut from a fractionator downstream of a hydrocracker unit. In another embodiment, an effluent from one or more naphtha reforming stage(s) of a multistage reformer are separated by fractional distillation to give at least one fraction containing at least 10 wt. % paraffinic $C_8$ hydrocarbons. The $C_8$ paraffinic feedstock has a boiling range from about 50° F. to about 550° F. and often from about 70° F. to about 450° F. The paraffinic $C_8$ containing feedstock can comprise, for example, straight run naphthas, paraffinic raffinates from aromatic extraction or adsorption, and $C_6$-$C_{10}$ paraffin-containing feeds, bioderived naphtha, naphtha from hydrocarbon synthesis processes, including Fischer Tropsch and methanol synthesis processes, as well as naphtha products from other refinery processes, such as hydrocracking or even conventional reforming.

In the process of the invention, the $C_8$ containing paraffinic feedstock is contacted with a catalyst containing a medium pore zeolite under reforming reaction conditions. The catalyst is such that para-xylene to meta-xylene molar ratio in the product is greater than the PX/MX thermodynamic equilibrium ratio. Compared to a thermodynamic equilibrium xylene mixture in which the para-xylene to meta-xylene ratio is approximately 0.5:1, the process described herein affords a product having a para-xylene to meta-xylene ratio of greater than 0.9:1. In illustrative embodiments, the product has a para-xylene to meta-xylene molar ratio of greater than 1:1, or greater than 1.1:1 or even greater than 1.2:1. The improved para-xylene yield reduces the cost of production and also minimizes the cost of separation of para-xylene from other xylene isomers and ethylbenzene, which is the most expensive step in many methods currently employed for producing para-xylene.

Definitions

The following terms will be used throughout the specification and will have the following meanings unless otherwise indicated.

As used herein, the terms "hydrocarbon" or "hydrocarbonaceous" or "petroleum" are used interchangeably to refer to carbonaceous material originating from crude oil, natural gas or biological processes.

As used herein "Group VIB" or "Group VIB metal" refers to one or more metals, or compounds thereof, selected from Group VIB of the Chemical Abstract Services Periodic Table. The Chemical Abstract Services Periodic Table may be found, for example, behind the front cover of CRC Handbook of Chemistry and Physics, 81$^{st}$ Edition, 2000-2001.

As used herein "Group VIII" or "Group VIII metal" refers to one or more metals, or compounds thereof, selected from Group VIII of the Chemical Abstract Services Periodic Table.

Hydrocracking is a chemical reaction of liquid feed materials, including hydrocarbons, petroleum and other biologically derived material, in the presence of hydrogen and one or more catalysts, resulting in product molecules having reduced molecular weight relative to that of the liquid feed materials. Additional reactions, including olefin and aromatic saturation and heteroatom (including oxygen, nitrogen, sulfur and halogen) removal may also occur during hydrocracking.

Reforming is a chemical reaction of liquid feed materials, including hydrocarbons, petroleum and other biological derived material, in the presence of one or more catalysts, resulting in product molecules such as automobile fuel, aromatics (for example benzene, toluene, xylenes and ethylbenzene), and/or hydrogen. Reactions typically involved in catalytic reforming include dehydrocylization, isomerization and dehydrogenation of naphtha range hydrocarbons, with dehydrocyclization and dehydrogenation of linear and slightly branched alkanes and dehydrogenation of cycloparaffins leading to the production of aromatics.

As used herein, a paraffin refers to a non-cyclic, linear or branched saturated hydrocarbon. For example, a $C_8$ paraffin is a non-cyclic, linear or branched hydrocarbon having 8 carbon atoms per molecule. Normal octane, methylheptanes, dimethylhexanes, trimethylpentanes are examples of $C_8$ paraffins. A paraffin-containing feed comprises non-cyclic saturated hydrocarbons, such as normal paraffins, isoparaffins, and mixtures thereof.

As used herein, a naphthene is a type of alkane having one or more rings of carbon atoms in its chemical structure. In embodiments, the naphthene is a cyclic, non-aromatic hydrocarbon. In some such embodiments, the naphthene is saturated. In some such embodiments, the naphthene is a cyclic, non-aromatic, saturated hydrocarbon having in the range of 5 to 8 carbon atoms in the cycle structure.

As used herein, naphtha is a distillate hydrocarbonaceous fraction boiling within the range of from 50° to 550° F. In some embodiments, naphtha boils within the range of 70° to 450° F., and more typically within the range of 80° to 400° F., and often within the range of 90° to 360° F. In some embodiments, at least 85 vol. % of naphtha boils within the range of from 50° to 550° F., and more typically within the range of from 70° to 450° F. In embodiments, at least 85 vol. % of naphtha is in the $C_4$-$C_{12}$ range, and more typically in the $C_5$-$C_{11}$ range, and often in the $C_6$-$C_{10}$ range. Naphtha can include, for example, straight run naphthas, paraffinic raffinates from aromatic extraction or adsorption, $C_6$-$C_{10}$ paraffin containing feeds, bioderived naphtha, naphtha from hydrocarbon synthesis processes, including Fischer Tropsch and methanol synthesis processes, as well as naphtha from other refinery processes, such as hydrocracking or conventional reforming.

As disclosed herein, boiling point temperatures are based on the ASTM D-2887 standard test method for boiling range distribution of petroleum fractions by gas chromatography, unless otherwise indicated. The mid-boiling point is defined as the 50% by volume boiling temperature, based on an ASTM D-2887 simulated distillation.

As disclosed herein, carbon number values (i.e. $C_5$, $C_6$, $C_8$, $C_9$ and the like) of hydrocarbons may be determined by standard gas chromatography methods.

Unless otherwise specified, feed rate to a catalytic reaction zone is reported as the volume of feed per hour per volume of catalyst. In effect, the feed rate as disclosed herein, referred to as liquid hourly space velocity (LHSV), is reported in reciprocal hours (i.e. $hr^{-1}$).

The term "silica to alumina ratio" refers to the molar ratio of silicon oxide ($SiO_2$) to aluminum oxide ($Al_2O_3$). ICP analysis may be used to determine silica to alumina ratio.

As used herein, the value for octane refers to the research octane number (RON), as determined by ASTM D2699-09.

As used herein, the quantity of pressure in units of psig (pounds per square inch gauge) is reported as "gauge" pressure, i.e. the absolute pressure minus the ambient pressure, unless otherwise indicated. The quantity of pressure in units of either psi (pounds per square inch) or kPa (kilopascals) is reported as absolute pressure, unless otherwise indicated.

As used herein "penultimate stage" does not refer necessarily to the second to last stage in a multistage reforming process but rather refers to a stage preceding at least one additional stage. As used herein "final stage" does not refer necessarily to the last stage of a multi stage reforming process but rather refers to the stage after a penultimate stage.

The equilibrium reaction for the conversion of toluene to xylene and benzene products normally yields about 24 wt. % para-xylene (PX), about 54 wt. % meta-xylene (MX), and about 22 wt. % ortho-xylene (OX) among xylenes. For a more complete description of equilibrium product distributions for xylene isomerization see R. D. Chirico and W. V. Steele, "Thermodynamic Equilibria in xylene isomerization. 5. Xylene isomerization equilibria from thermodynamic studies and reconciliation of calculated and experimental product distributions", *Journal of Chemical Engineering Data*, 1997, 42 (4), 784-790, herein incorporated by reference in its entirety.

The catalysts employed in the process of the invention may be employed in the form of pills, pellets, granules, broken fragments, or various special shapes, disposed as a fixed bed within a reaction zone, and the charging stock may be passed there through in the liquid, vapor, or mixed phase, and in either upward, downward or radial flow. Alternatively, they can be used in moving beds or in fluidized-solid processes, in which the charging stock is passed upward through a turbulent bed of finely divided catalyst. However, a fixed bed system or a dense-phase moving bed system are preferred due to the lower catalyst attrition losses and other operational advantages. In a fixed bed system, the feed can be preheated (by any suitable heating means) to the desired reaction temperature and then passed into a reaction zone containing a fixed bed of the catalyst. This reaction zone may be one or more separate reactors.

Hydrocracking

The hydrocracking reaction zone is maintained at conditions sufficient to effect a boiling range conversion of the hydrocarbonaceous feed to the hydrocracking reaction zone, so that the liquid hydrocrackate recovered from the hydrocracking reaction zone has a normal boiling point range below the boiling point range of the feed. The hydrocracking step reduces the size of the hydrocarbon molecules, hydrogenates olefin bonds, hydrogenates aromatics, and removes traces of heteroatoms resulting in an improvement in fuel or base oil product quality.

The hydrocracking catalyst generally comprises a cracking component, a hydrogenation component and a binder. Such catalysts are well known in the art. The cracking component may include an amorphous silica/alumina phase and/or a zeolite, such as a Y-type or USY zeolite. If present, the zeolite is at least about 1 percent by weight based on the total weight of the catalyst. A zeolite containing hydrocracking catalyst generally contains in the range of from 1 wt. % to 99 wt. % zeolite, and more typically in the range of 2 wt. % to 70 wt. % zeolite. Actual zeolite amounts will, of course be adjusted to meet catalytic performance requirements. The binder is generally silica or alumina. The hydrogenation component will be a Group VI, Group VII, or Group VIII metal or oxides or sulfides thereof, preferably one or more of molybdenum, tungsten, cobalt, or nickel, or the sulfides or oxides thereof. If present in the catalyst, these hydrogenation components generally make up from about 5% to about 40% by weight of the catalyst. Alternatively, platinum group metals, especially platinum and/or palladium, may be present as the hydrogenation component, either alone or in combination with the base metal hydrogenation components molybdenum, tungsten, cobalt, or nickel. If present, the platinum group metals will generally make up from about 0.1% to about 2% by weight of the catalyst.

The process of the invention can employ a wide variety of hydrocarbonaceous feedstocks from many different sources, such as crude oil, virgin petroleum fractions, recycle petroleum fractions, shale oil, liquefied coal, tar sand oil, synthetic paraffins from normal alphaolefin, recycled plastic feedstocks, petroleum distillates, solvent-deasphalted petroleum residua, shale oils, coal tar distillates, hydrocarbon feedstocks derived from plant, animal, and/or algal sources, and combinations thereof. Other feedstocks that can be used in the process of the invention include synthetic feeds, such as those derived from a Fischer Tropsch processes. Other suitable feedstocks include those heavy distillates normally defined as heavy straight-run gas oils and heavy cracked cycle oils, as well as conventional fluid catalytic cracking feed and portions thereof. In general, the feed can be any carbon containing feedstock susceptible to hydroprocessing catalytic reactions, particularly hydrocracking and/or reforming reactions. A suitable liquid hydrocracker feedstock is a vacuum gas oil boiling in a temperature range above about 450° F. (232° C.) and more typically within the temperature range of 550°-1100° F. (288-593° C.). In embodiments, at least 50 wt. % of the hydrocarbonaceous feedstock boils above 550° F. (288° C.). The term liquid refers to hydrocarbons, which are liquid at ambient conditions.

The liquid hydrocracker feedstock, which may be used in the instant invention, contains impurities such as nitrogen and sulfur, at least some of which are removed from the hydrocarbonaceous feedstock in the hydrocracking zone. Nitrogen impurities present in the hydrocarbonaceous feedstock may be present as organonitrogen compounds, in amounts greater than 1 ppm. Sulfur impurities may also be present. Feeds with high levels of nitrogen and sulfur, including those containing up to 0.5 wt % (and higher) nitrogen and up to 2 wt % and higher sulfur may be treated in the present process. However, feedstocks which are high in asphaltenes and metals will usually require some kind of prior treatment, such as in a hydrotreating operation, before they are suitable for use as a feedstock for the hydrocracking process step. A suitable liquid hydrocarbon feedstock generally contains less than about 500 ppm asphaltenes, more typically less than about 200 ppm asphaltenes, and often less than about 100 ppm asphaltenes.

According to one embodiment, the hydrocarbonaceous feedstock is placed in contact with the hydrocracking catalyst in the presence of hydrogen, usually in a fixed bed reactor in the hydrocracking reaction zone. The conditions of the hydrocracking reaction zone may vary according to the nature of the feed, the intended quality of the products, and the particular facilities of each refinery. Hydrocracking reaction conditions include, for example, a reaction temperature within the range of 450° F. to 900° F. (232° C.-482° C.), and typically a reaction temperature in the range of 650° F. to 850° F. (343° C.-454° C.); a reaction pressure within the range of 500 to 5000 psig (3.5-34.5 MPa), and typically a reaction pressure in the range of 1500-3500 psig (10.4-24.2 MPa); a liquid reactant feed rate, in terms of liquid hourly space velocity (LHSV) within the range of 0.1 to 15 hr$^{-1}$ (v/v), typically in the range of 0.25 to 2.5 hr$^{-1}$; and hydrogen feed rate, in terms of H$_2$/hydrocarbon ratio, is within the range of 500 to 5000 standard cubic feet per barrel of liquid hydrocarbon feed (89.1-445 m$^3$ H$_2$/m$^3$ feed). The hydrocrackate is then separated into various boiling range fractions. The separation is typically conducted by fractional distillation preceded by one or more vapor-liquid separators to remove hydrogen and/or other tail gases.

In some situations, the hydrocracking reaction conditions are established to achieve a target conversion of the hydrocarbonaceous feedstock within the hydrocracking reaction zone. For example, the hydrocracking reaction conditions may be set to achieve a conversion of greater than 30%. As an example, the target conversion may be greater than 40% or 50% or even 60%. As used herein, conversion is based on a reference temperature, such as, for example, the minimum boiling point temperature of the hydrocracker feedstock. The extent of conversion relates to the percentage of feed boiling above the reference temperature which is converted to products boiling below the reference temperature.

The hydrocracking reaction zone that contains the hydrocracking catalyst may be contained within a single reactor vessel, or it may be contained in two or more reactor vessels, connected together in fluid communication in a serial arrangement. In embodiments, hydrogen and the hydrocarbonaceous feed are provided to the hydrocracking reaction zone in combination. Additional hydrogen may be provided at various locations along the length of the reaction zone to maintain an adequate hydrogen supply to the zone. Furthermore, relatively cool hydrogen added along the length of the reactor may serve to absorb some of the heat energy within the zone, and help to maintain a relatively constant temperature profile during the exothermic reactions occurring in the reaction zone.

Catalysts within the hydrocracking reaction zone may be of a single type. In embodiments, multiple catalyst types may be blended in the reaction zone, or they may be layered in separate catalyst layers to provide a specific catalytic function that provides improved operation or improved product properties. The catalyst may be present in the reaction zone in a fixed bed configuration, with the hydrocarbonaceous feed passing either upward or downward through the zone. In embodiments, the hydrocarbonaceous feed passes co-currently with the hydrogen feed within the zone. In other embodiments, the hydrocarbonaceous feed passes counter-current to the hydrogen feed within the zone.

The effluent from the hydrocracking reaction zone is the total of materials passing from the hydrocracking reaction zone, and generally includes normally liquid hydrocarbonaceous materials, normally gas phase hydrocarbonaceous reaction products, one or more of H$_2$S, NH$_3$ and H$_2$O from reaction of heteroatoms with hydrogen in the reaction zone and unreacted hydrogen.

In general, the hydrocracking reaction zone effluent is first processed to recover at least a portion of the unreacted hydrogen in one or more initial separation steps, using flash separation or fractional distillation processes. These initial separation steps are well known, and their design and operation are dictated by the specific process requirements. The flash separation steps are usually operated at a pressure within the range of from ambient pressure up to the pressure of the hydrocracking reaction zone, and at a temperature within the range of 100° F. up to the hydrocracking reaction zone temperature.

At least a portion of the effluent from the hydrocracking reaction zone is separated by means of fractional distillation into various fractions based on the initial and final boiling points of the components. In embodiments, the separation is conducted in an atmospheric distillation column, operated at a pressure of roughly equal to or slightly above ambient pressures, including a pressure from 0 psig to 100 psig. Distillate fractions from an atmospheric column may include one or more of $C_4$– fractions, $C_5$-$C_8$ fraction, and one or more $C_9$+ fractions, with each fraction being distinguished by a unique boiling point range. Such atmospheric distillation processes are well known. In embodiments, the bottoms fraction from the atmospheric distillation is further separated in a vacuum distillation column, operated at subatmospheric pressure. Distillate fractions from vacuum distillation include one or more vacuum gas oil fractions, boiling within a range of from approximately 500°-1100° F. In general, a distillate fraction recovered from the distillation is in the vapor phase at the conditions of the distillation but in the liquid phase at ambient conditions; a gaseous overhead fraction recovered from the distillation is in the vapor phase at the conditions of the distillation and also in the vapor phase at ambient conditions; and a bottoms fraction recovered from the distillation remains in the liquid phase at the conditions of the distillation.

In embodiments, the $C_8$ containing paraffin feedstock is a hydrocracked naphtha. An exemplary hydrocracked naphtha that is useful in the process is recovered from the atmospheric distillation of at least a portion of the effluent from the hydrocracking reaction zone. Exemplary hydrocracked naphthas that are recovered from atmospheric distillation generally have a normal boiling point range within the range of from 50° to 550° F. and more typically within the range of from 70° to 450° F. The distillation may be generally operated to produce a naphtha stream comprising at least 60 wt. % $C_4$ to $C_{10}$ hydrocarbons, more typically at least 70 wt. % $C_4$ to $C_{10}$ hydrocarbons, and often at least 80 wt. % $C_4$ to $C_{10}$ hydrocarbons. In embodiments, the distillation may be generally operated to produce a naphtha stream comprising at least 60 wt. % $C_5$ to $C_9$ hydrocarbons, more typically at least 70 wt. % $C_5$ to $C_9$ hydrocarbons and often at least 80 wt. % $C_5$ to $C_9$ hydrocarbons. In embodiments, the distillation may be generally operated to produce a naphtha stream comprising at least 60 wt. % $C_6$ to $C_8$ hydrocarbons, more typically at least 70 wt. % $C_6$ to $C_8$ hydrocarbons, and often at least 80 wt. % wt. % $C_6$ to $C_8$ hydrocarbons.

In an embodiment, the hydrocracked naphtha generally contains at least about 5 wt. % paraffinic $C_8$ hydrocarbons, more typically at least about 10 wt. % paraffinic $C_8$ hydrocarbons, and often at least about 12 wt. % paraffinic $C_8$ hydrocarbons, or at least about 15 wt. % paraffinic $C_8$ hydrocarbons. In a separate embodiment, the hydrocracked naphtha generally contains at least about 40 wt. % paraffinic $C_8$ hydrocarbons, more typically at least about 50 wt. % paraffinic $C_8$ hydrocarbons and often at least about 60 wt. % paraffinic $C_8$ hydrocarbons. Tailoring the hydrocracked naphtha to yield a desired paraffinic $C_8$ hydrocarbon content is achieved, at least in part, by selection of the distillation design and operating parameters.

In embodiments, the hydrocracked naphtha contains less than 10 wt. % aromatics, more typically less than 5 wt. % aromatics, and often less than 2 wt. % aromatics. In embodiments, the hydrocracked naphtha contains less than 1000 ppm sulfur, more typically less than 100 ppm sulfur, and often less than 10 ppm sulfur and even less than 1 ppm sulfur. In embodiments, the hydrocracked naphtha contains less than 1000 ppm nitrogen, more typically less than 100 ppm nitrogen, and often less than 10 ppm nitrogen and even less than 1 ppm nitrogen. In embodiments, the hydrocracked naphtha has an octane number of less than 90, more typically less than 85, often less than 80, and even less than 75.

Reforming

The reforming catalyst is selected to provide a high selectivity for the production of aromatic compounds at a reduced pressure, which increases the selectivity of $C_6$ to $C_8$ paraffin dehydrocyclization while maintaining low catalyst fouling rates. In embodiments, the reforming catalyst comprises at least one medium pore zeolite. The molecular sieve is a porous inorganic oxide characterized by a crystalline structure which provides pores of a specified geometry, depending on the particular structure of each molecular sieve. The phrase "medium pore" as used herein means having a crystallographic free diameter in the range of from about 3.9 to about 7.1 Angstrom when the porous inorganic oxide is in the calcined form. The crystallographic free diameters of the channels of molecular sieves are published in the "Atlas of Zeolite Framework Types", Fifth Revised Edition, 2001, by Ch. Baerlocher, W. M. Meier, and D. H. Olson, Elsevier, pp 10-15, which is incorporated herein by reference. Non-limiting examples of medium pore zeolites include ZSM-5, ZSM-11, ZSM-22, ZSM-23, ZSM-35, ZSM-38, ZSM-48 MCM-22, SSZ-20, SSZ-25, SSZ-32, SSZ-35, SSZ-37, SSZ-44, SSZ-45, SSZ-47, SSZ-58, SSZ-74, SUZ-4, EU-1, NU-85, NU-87, NU-88, IM-5, TNU-9, ESR-10, TNU-10 and combinations thereof. In embodiments, the medium pore zeolite is a zeolite, which is a crystalline material that possess three-dimensional frameworks composed of tetrahedral units ($TO_{4/2}$, T=Si, Al, or other tetrahedrally coordinated atom) linked through oxygen atoms. A medium pore zeolite that is useful in the present process includes ZSM-5. Various references disclosing ZSM-5 are provided in U.S. Pat. No. 4,401,555 to Miller. Additional disclosure on the preparation and properties of high silica ZSM-5 may be found, for example, in U.S. Pat. Nos. 5,407,558 and 5,376,259.

In embodiments, the reforming catalyst includes a silicate having a form of ZSM-5 with a molar ratio of $SiO_2/M_2O_3$ of at least 40:1, or at least 200:1 or at least 500:1, or even at least 1000:1, where M is selected from Al, B, or Ga. In embodiments, the ZSM-5 has a silica to alumina molar ratio of at least 40:1, or at least 200:1, or at least 500:1, or even at least 1000:1. The silicate that is useful further is characterized as having a crystallite size of less than 10 µm, or less than 5 µm or even less than 1 µm. Methods for determining crystallite size, using, for example Scanning Electron Microscopy, are well known. The silicate that is useful is further characterized as having at least 80% crystallinity, or at least 90% crystallinity, or at least 95% crystallinity. Methods for determining crystallinity, using, for example, X-ray Diffraction, are well known.

Strong acidity is undesirable in the catalyst because it promotes cracking, resulting in lower selectivity to $C_5$+ liquid product. To reduce acidity, a silicate that contains alkali metal and/or alkaline earth metal cations is useful for reforming the naphtha. The alkali or alkaline earth cations may be incorporated into the catalyst during or after synthesis of the molecular sieve. Suitable molecular sieves are characterized by having at least 90% of the acid sites, or at least 95% of the acid sites, or at least 99% of the acid sites being neutralized by introduction of the alkali or alkaline earth cations. In one embodiment, the medium pore zeolite contains less than 5000 ppm alkali. Such molecular sieves are disclosed, for example, in U.S. Pat. No. 4,061,724, in U.S. Pat. No. 5,182,012 and in U.S. Pat. No. 5,169,813. These patents are incorporated herein by reference, particularly with respect to the description, preparation and analysis of molecular sieves having the specified molar silica to alumina molar ratios, having a specified crystallite size, having a specified crystallinity and having a specified alkali and/or alkaline earth content.

In embodiments, the silicate is a ZSM-5 type medium pore zeolite. In some such embodiments, the silicate is silicalite, a very high ratio silica to alumina form of ZSM-5. In embodiments, the silicalite has a silica to alumina molar ratio of at least 40:1, or at least 200:1, or at least 500:1, or even at least 1000:1. Various references disclosing silicalite and ZSM-5 are provided in U.S. Pat. No. 4,401,555 to Miller and U.S. Pat. No. 6,063,723 to Miller. These references include the aforesaid U.S. Pat. No. 4,061,724 to Grose et al.; U.S. Pat. Reissue No. 29,948 to Dwyer et al.; Flanigen et al., Nature, 271, 512-516 (Feb. 9, 1978) which discusses the physical and adsorption characteristics of silicalite; and Anderson et al., J. Catalysis 58, 114-130 (1979) which discloses catalytic reactions and sorption measurements carried out on ZSM-5 and silicalite. The disclosures of these publications are incorporated herein by reference.

Other zeolites which can be used in the process of the present invention include those as listed in U.S. Pat. No. 4,835,336; namely: ZSM-11, ZSM-12, ZSM-22, ZSM-23, ZSM-35, ZSM-38, ZSM-48, and other similar materials.

ZSM-5 is more particularly described in U.S. Pat. No. 3,702,886 and U.S. Pat. No. Re. 29,948, the entire contents of which are incorporated herein by reference.

ZSM-11 is more particularly described in U.S. Pat. No. 3,709,979 the entire contents of which are incorporated herein by reference.

ZSM-12 is more particularly described in U.S. Pat. No. 3,832,449, the entire contents of which are incorporated herein by reference.

ZSM-22 is more particularly described in U.S. Pat. Nos. 4,481,177, 4,556,477 and European Patent No. 102,716, the entire contents of each being expressly incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

ZSM-48 is more particularly described in U.S. Pat. No. 4,397,827 the entire contents of which are incorporated herein by reference.

In embodiments, the crystalline silicate may be in the form of a borosilicate, where boron replaces at least a portion of the aluminum of the more typical aluminosilicate form of the silicate. Borosilicates are described in U.S. Pat. Nos. 4,268,420; 4,269,813; and 4,327,236 to Klotz, the disclosures of which patents are incorporated herein, particularly that disclosure related to borosilicate preparation. In a suitable borosilicate, the crystalline structure is that of ZSM-5, in terms of X-ray diffraction pattern. Boron in the ZSM-5 type borosilicates takes the place of aluminum that is present in the more typical ZSM-5 crystalline aluminosilicate structures. Borosilicates contain boron in place of aluminum, but generally there is some trace amounts of aluminum present in crystalline borosilicates.

Still further crystalline silicates which can be used in the present invention are ferrosilicates, as disclosed for example in U.S. Pat. No. 4,238,318, gallosilicates, as disclosed for example in U.S. Pat. No. 4,636,483, and chromosilicates, as disclosed for example in U.S. Pat. No. 4,299,808.

The reforming catalyst further contains one or more Group VIII metals, e.g., nickel, ruthenium, rhodium, palladium, iridium or platinum. In embodiments, the Group VIII metals include iridium, palladium, platinum or a combination thereof. These metals are more selective with regard to dehydrocyclization and are also more stable under the dehydrocyclization reaction conditions than other Group VIII metals. When employed in the reforming catalyst, these metals are generally present in the range of between 0.1 wt. % and 5 wt. % or between 0.3 wt. % to 2.5 wt. %. The catalyst may further comprise a promoter, such as rhenium, tin, germanium, cobalt, nickel, iridium, tungsten, rhodium, ruthenium, or combinations thereof. In an illustrative embodiment, the catalyst comprises in the range of 0.1 wt. % to 1 wt. % platinum and in the range of 0.1 wt. % to 1 wt. % rhenium.

In forming the reforming catalyst, the crystalline molecular sieve is preferably bound with a matrix. Satisfactory matrices include inorganic oxides, including alumina, silica, naturally occurring and conventionally processed clays, such as bentonite, kaolin, sepiolite, attapulgite and halloysite.

The actual reaction conditions employed in the process of the invention will depend, at least in part, on the feed used, whether highly aromatic, paraffinic or naphthenic. Reaction conditions of temperature, pressure, hydrocarbon to hydrogen ratio, and LHSV can be tuned in order to maximize para-xylene production.

The process for producing para-xylene includes reforming naphtha over a silicate catalyst. In one embodiment, the process of the invention for producing para-xylene can be incorporated into a multistage naphtha reforming process. The naphtha reforming conditions can be chosen such that the feedstock used in the process of the invention comprises at least about 10% $C_8$ paraffinic hydrocarbons. For example, the effluent from a penultimate stage of a multistage naphtha reforming process, wherein the effluent contains at least about 5 wt. % $C_8$ paraffinic hydrocarbons, or at least about 10 wt. % $C_8$ paraffinic hydrocarbons, or at least about 12 wt. % $C_8$ paraffinic hydrocarbons, or even at least about 15 wt. % $C_8$ paraffinic hydrocarbons, can be contacted with the catalyst used in the process of the invention in a separate stage at para-xylene-forming reaction conditions, including a temperature in the range from about 800° F. to about 1100° F., a pressure in the range from about 1 to about 1000 psig, or from about 0 psig to about 350 psig and a feed rate in the range of from about 0.1 $hr^{-1}$ to about 20 $hr^{-1}$ LHSV. Hydrogen may be added as an additional feed to the stage in which para-xylene is produced if required. Hydrogen can be generated by the process of the invention depending on the feedstock. This hydrogen can be recycled to the reformer as an added economic benefit. The process of the invention can be operated at conditions to maintain a molar $H_2$/hydrocarbon ratio in the range of 0.5:1 to 10:1. A molar $H_2$/hydrocarbon ratio in the range of 1:1 to 4:1 is exemplary.

In another embodiment, the process of the invention for producing para-xylene can be incorporated into a multistage naphtha reforming process after a separation stage, for example after a fractional distillation of effluent from a penultimate stage. For example, the effluent from a penultimate stage of a multistage naphtha reforming process can be separated into at least a $C_8$ containing stream via such processes as fractional distillation. The $C_8$ containing stream comprises at least about 5 wt. % $C_8$ paraffinic hydrocarbons, or at least about 10 wt. % $C_8$ paraffinic hydrocarbons, or at least about 12 wt. % $C_8$ paraffinic hydrocarbons, or even at least about 15 wt. % $C_8$ paraffinic hydrocarbons. This stream can be contacted with the catalyst used in the process of the invention in a separate stage at para-xylene-forming reaction conditions, as described above.

In an embodiment, the process of the present invention can be stand-alone. By "stand-alone" it is meant that the process of the invention is run in a separate reactor. Exemplary, non-limiting examples of feedstocks comprising at least about 10 wt. % $C_8$ paraffinic hydrocarbons include a naphtha fraction from a hydrocracking reactor, straight run naphtha fractions, naphthas derived from fluid catalytic cracking, or combinations thereof.

In yet another embodiment, the process of the invention can be integrated into a hydrocracking process. The hydrocracker can directly provide the $C_8$ containing paraffinic feedstock for the process of the invention. Generally, a hydrocracker can use a variety of hydrocarbonaceous feedstocks such as gas oils and heavy gas oils. A typical gas oil comprises a substantial portion of hydrocarbon components boiling above about 550° F., usually at least about 50 percent by weight boiling above 550° F. A typical vacuum gas oil normally has a boiling point range between about 600° F. and about 1050° F. The hydrocarbon feedstocks that may be subjected to hydrocracking by the hydrocracker include all mineral oils and synthetic oils (e.g., shale oil, tar sand products, etc.) and fractions thereof. Illustrative hydrocarbon feedstocks include those comprising components boiling above 550° F., such as atmospheric gas oils, vacuum gas oils, deasphalted, vacuum, and atmospheric residua, hydrotreated residual oils, coker distillates, straight run distillates, pyrolysis-derived oils, high boiling synthetic oils, various petroleum distillates, cycle oils and catalytic cracker distillates. The skilled practitioner will appreciate that the scope of the present process encompasses a number of specific hydrocracker process configurations, including single stage and two-stage hydrocracking, including once-through feed and recycle operation, and including the presence or absence of one or more distillation stages, including atmospheric pressure distillation and vacuum distillation.

Reference is now made to an embodiment of the invention illustrated in FIG. 1. A hydrocarbonaceous feedstock 2 which boils above about 550° F. passes into the reaction zone 10 and is contacted with a hydrocracking catalyst. The reaction zone 10 may contain one or more beds of the same or different catalyst. The hydrocracking of the hydrocarbonaceous feedstock 2 in contact with a hydrocracking catalyst in the reaction zone 10 is conducted in the presence of hydrogen and preferably at hydrocracking conditions which include a temperature from about 450° F. (232° C.) to about 900° F. (482° C.), a pressure from about 500 psig to about 5000 psig, a liquid hourly space velocity (LHSV) from about 0.1 to about 15 $hr^{-1}$, and a hydrogen circulation rate from about 500 to about 5,000 standard cubic feet per barrel. Hydrogen is introduced through a fresh hydrogen feed 4 and hydrogen recycle loop 42.

The effluent 12 from the hydrocracker reaction zone 10 comprises $C_8$ paraffinic hydrocarbons. In the embodiment illustrated in FIG. 1, the effluent is separated in separation zone 20 into a hydrogen-containing stream 22, one or more light streams 24 (comprising, for example, $C_7$- hydrocarbons), a $C_8$ containing hydrocarbon stream 26 (comprising at least about 10 wt. % $C_8$ paraffinic hydrocarbons), and one or more heavy streams 28 (comprising, for example, $C_{9+}$ hydrocarbons) and a bottoms stream 29. In embodiments, this separation occurs in a single separation zone using a fractionator. In other embodiments, this separation is done in sequential zones, with the hydrogen, and optionally the $C_4$- stream, separated in one or more preliminary separation zones prior to the separation of the $C_8$ containing hydrocarbon stream 26 and the heavy stream 28. Unreacted material can be recycled back to the reaction zone 10 or passed to an optional second reaction zone for further cracking. The $C_8$ containing hydrocarbon stream comprising at least about 10 wt. % $C_8$ paraffinic hydrocarbons is passed to a reforming reaction zone 40. The $C_8$ paraffinic hydrocarbons may be further heated prior to being passed to the para-xylene reaction zone. In the process of the invention, the $C_8$ paraffinic feed stream is contacted with a catalyst comprising a silicalite molecular sieve having a silica to alumina molar ratio of at least about 40 to 1. Reaction conditions for the para-xylene reaction zone include a pressure of between 0 psig to 350 psig, a temperature of between 800° F. to 1100° F., and a flow rate of between 0.1 $hr^{-1}$ to 20 $hr^{-1}$ LHSV.

The product stream 44 from the para-xylene reaction zone 40 comprises $C_8$ aromatic hydrocarbons including para-xylene and meta-xylene, in a para-xylene to meta-xylene weight ratio of at least 0.9. In embodiments, the para-xylene to meta-xylene weight ratio is at least 1.0, or at least 1.1 or at least 1.2. The para-xylene reaction zone also produces hydrogen 42. This hydrogen can be recycled to the hydrocracker reaction zone 10. The generation of hydrogen by the process of the invention provides an economic benefit by minimizing the additional hydrogen needed for the hydrocracking reaction zone. The para-xylene in the product stream 44 can be separated by any suitable method such as by passing the same through a water condenser and subsequently passing the organic phase through a column in which chromatographic separation of the xylene isomers is accomplished. Another method of separating the para-xylene from other isomers and hydrocarbon compounds is crystallization wherein the para-xylene containing product is cooled to afford predominantly crystals of para-xylene, the para-xylene containing stream 54 is removed by any suitable means such as filtration and/or centrifugation. The remaining hydrocarbons can be recycled as $C_8$ feedstock for the process of the invention. The para-xylene thus formed can be separated as described above by filtration and/or centrifugation, for example. The para-xylene depleted product stream 52 can then be recycled back to the reforming reaction zone for further processing.

The process of the invention can be repeated in subsequent reaction rounds until the $C_8$ containing feedstock is depleted in $C_8$ paraffinic hydrocarbons such that the feedstock comprises less than 5 wt. % $C_8$ paraffinic hydrocarbons.

The following examples are presented to exemplify embodiments of the invention but are not intended to limit the invention to the specific embodiments. Unless indicated to the contrary, all parts and percentages are by weight. All numerical values are approximate. When numerical ranges are given, it should be understood that embodiments outside the stated ranges may still fall within the scope of the invention. Specific details described in each example should not be construed as necessary features of the invention.

EXAMPLES

Example 1

A naphtha feedstock comprising greater than 10% C8 paraffinic hydrocarbons, with an ASTM D-2887 simulated distillation shown in Table 1, was used as feed for the process of the invention and the following comparative examples (IBP=initial boiling point, EP=end boiling point). The feedstock composition was characterized by API, RON, and GC analysis with results given in Table 2, where B stands for benzene, T for toluene, X for all three xylene isomers and EB for ethylbenzene while PX/MX stands for the yield ratio of para-xylene to meta-xylene.

TABLE 1

ASTM D-2887 simulated distillation of the feed

| Vol. % | Temperature, ° F. |
|---|---|
| IBP | 77 |
| 10 | 168 |
| 30 | 218 |
| 50 | 246 |
| 70 | 273 |
| 90 | 302 |
| EP | 331 |

TABLE 2

Other properties of the feed

| API | 57.7 |
|---|---|
| RON | 65.9 |
| $C_5+$, wt. % | 99.9 |
| Benzene, wt. % | 0.5 |
| Toluene, wt. % | 1.7 |
| Ethylbenzene, wt. % | 1.7 |
| m-Xylene, wt. % | 1.1 |
| p-Xylene, wt. % | 0.5 |
| o-Xylene, wt. % | 1.1 |
| Total BTX + EB, wt. % | 4.9 |
| PX/MX | 0.46 |
| Total $C_8$, wt. % | 25.4 |
| $C_8$ paraffins, wt. % | 13.7 |
| $C_8$ naphthenes, wt. % | 7.3 |

Example 2

Comparative

The naphtha feed described in Example 1 was contacted in a fixed-bed reactor containing a commercial amorphous reforming catalyst comprising platinum with a rhenium promoter on an alumina support. The reaction conditions included the temperatures of 885, 895, 905 and 915° F., a pressure of 350 psig, a liquid hourly space velocity (LHSV) of 1.5 $hr^{-1}$ and a molar ratio of hydrogen to hydrocarbon of 5:1.

The yield of $C_5+$ liquid, its RON and other properties as well as the hydrogen production obtained under the aforementioned conditions are listed in Table 3, where HC stands for hydrocarbons and $H_2$/HC for the molar ratio of hydrogen to hydrocarbon at the reactor inlet. A PX/MX ratio of about 0.41 was obtained for all the products at these four temperatures.

TABLE 3

Properties of reforming products obtained from a commercial reforming catalyst comprising platinum with a rhenium promoter on an alumina support.

| Pressure, psig | 350 | | | |
|---|---|---|---|---|
| LHSV, $hr^{-1}$ | 1.5 | | | |
| H2/HC | 5:1 | | | |
| Temperature, ° F. | 885 | 895 | 905 | 915 |
| RON | 93.7 | 94.9 | 95.7 | 96.8 |
| $C_5+$, wt. % | 90.3 | 89.2 | 88.9 | 88.6 |
| Benzene, wt. % | 3.9 | 4.2 | 4.4 | 4.6 |
| Toluene, wt. % | 14.5 | 15.0 | 15.1 | 15.4 |
| Ethylbenzene, wt. % | 2.7 | 2.8 | 2.9 | 3.1 |
| m-Xylene, wt. % | 9.1 | 9.3 | 9.3 | 9.3 |

TABLE 3-continued

Properties of reforming products obtained from a commercial reforming catalyst comprising platinum with a rhenium promoter on an alumina support.

| p-Xylene, wt. % | 3.7 | 3.7 | 3.8 | 3.8 |
|---|---|---|---|---|
| o-Xylene, wt. % | 4.3 | 4.4 | 4.4 | 4.4 |
| Total BTX + EB, wt. % | 38.2 | 39.4 | 39.9 | 40.6 |
| PX/MX | 0.41 | 0.40 | 0.41 | 0.41 |
| $H_2$ Production, standard cubic feet per barrel feed | 950 | 990 | 1000 | 1050 |

Example 3

Invention

The naphtha feed described in Example 1 was contacted in a fixed-bed reactor containing a ZSM-5 zeolite based catalyst composited with 30 wt. % alumina binder material. The ZSM-5 had a $SiO_2/Al_2O_3$ molar ratio of about 500 and was ion exchanged to the ammonium form before incorporating in a 70 wt. % zeolite on 30 wt. % alumina extrudate. The extrudate was impregnated with 0.8 wt. % Pt, 0.38 wt. % Re, 0.35 wt. % Na and 0.3 wt. % Mg by an incipient wetness procedure to make the final catalyst. The reaction conditions included the temperatures of 865, 875, 885, 895, 905 and 915° F., a pressure of 80 psig, a liquid hourly space velocity (LHSV) of 1.0 $hr^{-1}$ and a molar ratio of hydrogen to hydrocarbon of 2:1.

The yield of $C_5+$ liquid, its RON and other properties as well as the hydrogen production obtained under the aforementioned conditions are listed in Table 4. The PX/MX ratio of the products produced over the ZSM-5 zeolite based catalyst in this example ranged from 1.02 to 1.32.

TABLE 4

Properties of reforming products obtained from a ZSM-5 based catalyst.

| Pressure, psig | 80 | | | | | |
|---|---|---|---|---|---|---|
| LHSV, $hr^{-1}$ | 1.0 | | | | | |
| $H_2$/HC | 2:1 | | | | | |
| Temperature, ° F. | 865 | 875 | 885 | 895 | 905 | 915 |
| RON | 91.1 | 91.7 | 93.3 | 94.7 | 97.0 | 98.1 |
| $C_5+$, wt. % | 92.8 | 92.2 | 91.2 | 89.8 | 87.7 | 86.5 |
| Benzene, wt. % | 3.4 | 3.7 | 4.0 | 4.4 | 4.6 | 5.3 |
| Toluene, wt. % | 13.6 | 14.2 | 15.0 | 15.8 | 17.0 | 17.7 |
| Ethylbenzene, wt. % | 3.5 | 3.6 | 3.7 | 3.8 | 4.2 | 4.2 |
| m-Xylene, wt. % | 5.0 | 5.2 | 5.3 | 5.5 | 6.2 | 6.3 |
| p-Xylene, wt. % | 6.6 | 6.7 | 6.8 | 6.8 | 6.4 | 6.4 |
| o-Xylene, wt. % | 2.4 | 2.5 | 2.5 | 2.6 | 2.8 | 2.9 |
| Total BTX + EB, wt. % | 34.5 | 35.9 | 37.3 | 38.9 | 41.2 | 42.8 |
| PX/MX | 1.32 | 1.29 | 1.28 | 1.24 | 1.03 | 1.02 |
| $H_2$ Production, standard cubic feet per barrel feed | 890 | 910 | 960 | 1000 | 1030 | 1060 |

Example 4

Invention

A naphtha feed is prepared in a distillation process suited for producing a naphtha feed having a high amount of $C_8$ hydrocarbons. In this example, the naphtha feed contains greater than 40 wt. % $C_8$ hydrocarbons, of which greater than 40 wt. % are $C_8$ paraffins. The para-xylene/meta-xylene wt. ratio of the naphtha feed is in the range of 0.4-0.45. This naphtha feed is contacted in a fixed-bed reactor containing a ZXM-5 zeolite based catalyst as described in Example 3. The para-xylene/meta-xylene molar ratio of the reformed products is greater than 1.0.

As demonstrated in the above examples, the process of the invention provides increased para-xylene yield as compared with a conventional process for making para-xylene. The process of the invention also gave a much higher PX/MX ratio compared to the comparative example process. Comparing the PX/MX ratios in Tables 3 and 4, clearly demonstrates the para-selectivity of the ZSM-5 zeolite based catalyst used in the process of the invention.

What is claimed is:

1. A process for producing para-xylene comprising the steps of:
    (a) contacting a hydrocarbonaceous feed wherein at least 50 wt. % of said feed boils above 550° F., in a first reaction zone comprising a hydrocracking catalyst under hydrocracking conditions to form an effluent;
    (b) separating the effluent into at least a $C_8$ containing fraction comprising at least 10 wt. % $C_8$ paraffinic hydrocarbons;
    (c) providing the $C_8$ containing fraction to a second reaction zone;
    (d) contacting the $C_8$ containing fraction under reforming reaction conditions with a reforming catalyst comprising a medium pore zeolite having a silica to alumina molar ratio of at least 200, a crystallite size of less than 10 microns and an alkali content of less than 5000 ppm in a second reaction zone to produce a product stream comprising para-xylene and meta-xylene wherein the para-xylene to meta-xylene ratio is at least 0.9, where the medium pore zeolite is selected from the group consisting of ZSM-5, ZSM-11, ZSM-12, ZSM-22, ZSM-23, ZSM-35, ZSM-38, ZSM-48, MCM-22, SSZ-20, SSZ-25, SSZ-32, SSZ-35, SSZ-37, SSZ-44, SSZ-45, SSZ-47, SSZ-58, SSZ-74, SUZ-4, EU-1, NU-85, NU-87, NU-88, IM-5, TNU-9, ESR-10, TNU-10, and combinations thereof; and
    (e) separating the para-xylene from the product stream.

2. The process of claim 1, wherein the medium pore zeolite is selected from the group consisting of ZSM-5, ZSM-11, ZSM-12, ZSM-22, ZSM-23, ZSM-35, ZSM-38, ZSM-48, and combinations thereof.

3. The process of claim 1, wherein the medium pore zeolite is ZSM-5.

4. The process of claim 3, wherein the ZSM-5 has a silica to alumina molar ratio of at least 500.

5. The process of claim 1, wherein the reforming catalyst comprises a medium pore zeolite having a silica to alumina molar ratio of at least 200, a crystallite size of less than 10 microns, an alkali content of less than 5000 ppm and in the range of between 0.1 wt. % and 1 wt. % of platinum, rhenium, or combinations thereof.

6. The process of claim 1, wherein step (d) further comprises producing para-xylene and meta-xylene in the weight ratio of at least 1.0.

7. The process of claim 1, wherein step (d) further comprises producing para-xylene and meta-xylene in the weight ratio of at least 1.1.

8. The process of claim 1, wherein step (d) further comprises producing para-xylene and meta-xylene in the weight ratio of at least 1.2.

9. The process of claim 1, wherein step (e) comprises separating the para-xylene from the product stream by crystallization.

10. The process of claim 1, wherein the hydrocracking conditions comprise a temperature of between 450 to 900° F., a pressure between 500 to 5000 psig, a LHSV between 0.1 to 15 and a hydrogen circulation rate between 2000 to 5,000 standard cubic feet per barrel.

11. The process of claim 1, further comprising the step of recovering a para-xylene depleted product stream.

12. The process of claim 11, further comprising the step of recycling the para-xylene depleted product stream to the second reaction zone.

13. The process of claim 1, wherein the reforming reaction conditions include a pressure of between 0 psig to 350 psig, a temperature of between 800° F. to 1100° F., and a flow rate of between 0.1 hr$^{-1}$ to 20 hr$^{-1}$ LHSV.

14. The process of claim 1, further comprising generating hydrogen from the second reaction zone.

15. The process of claim 14, wherein the hydrogen is recycled to the first reaction zone.

16. The process of claim 1, wherein the $C_8$ containing fraction has a boiling range from about 50° F. to about 550° F.

17. The process of claim 1, wherein the hydrocracking catalyst comprises a cracking component, a hydrogenation component, and a binder.

18. The process of claim 1, wherein the hydrocracking conditions achieve a conversion of greater than 40%.

19. A process for producing para-xylene comprising the steps of:
    (a) contacting a hydrocarbonaceous feed wherein at least 50 wt. % of said feed boils above 550° F., in a first reaction zone comprising a hydrocracking catalyst under hydrocracking conditions to form an effluent;
    (b) separating the effluent into at least a $C_8$ containing fraction comprising at least 10 wt. % $C_8$ paraffinic hydrocarbons;
    (c) providing the $C_8$ containing fraction to a second reaction zone;
    (d) contacting the $C_8$ containing fraction under reforming reaction conditions with a reforming catalyst comprising a medium pore zeolite having a silica to alumina molar ratio of at least 200, a crystallite size of less than 10 microns and an alkali content of less than 5000 ppm in a second reaction zone to produce a product stream comprising para-xylene and meta-xylene wherein the para-xylene to meta-xylene ratio is at least 0.9, where the reforming catalyst comprises silicate; and
    (e) separating the para-xylene from the product stream.

20. The process of claim 19, wherein the reforming catalyst comprises a medium pore zeolite having a silica to alumina molar ratio of at least 200, a crystallite size of less than 10 microns, an alkali content of less than 5000 ppm and in the range of between 0.1 wt. % and 1 wt. % of platinum, rhenium, or combinations thereof.

21. The process of claim 19, wherein step (d) further comprises producing para-xylene and meta-xylene in the weight ratio of at least 1.0.

22. The process of claim 19, wherein the hydrocracking conditions comprise a temperature of between 450 to 900° F., a pressure between 500 to 5000 psig, a LHSV between 0.1 to 15 and a hydrogen circulation rate between 2000 to 5,000 standard cubic feet per barrel.

23. The process of claim 19, further comprising recovering a para-xylene depleted product stream and recycling the para-xylene depleted product stream to the second reaction zone.

24. The process of claim 19, wherein the reforming reaction conditions include a pressure of between 0 psig to 350 psig, a temperature of between 800° F. to 1100° F., and a flow rate of between 0.1 $hr^{-1}$ to 20 $hr^{-1}$ LHSV.

25. The process of claim 19, further comprising generating hydrogen from the second reaction zone.

26. The process of claim 19, wherein the hydrocracking catalyst comprises a cracking component, a hydrogenation component, and a binder.

27. The process of claim 19, wherein the hydrocracking conditions achieve a conversion of greater than 40%.

\* \* \* \* \*